United States Patent [19]

Crane et al.

[11] Patent Number: 4,544,246

[45] Date of Patent: Oct. 1, 1985

[54] SYSTEM FOR PRODUCING SELECTIVE STABILIZATION OF A PORTION OF THE RETINAL IMAGE

[75] Inventors: Hewitt D. Crane, Portola Valley; Donald H. Kelly, Los Altos Hills, both of Calif.

[73] Assignee: SRI International, Menlo Park, Calif.

[21] Appl. No.: 503,800

[22] Filed: Jun. 13, 1983

[51] Int. Cl.$^4$ .............................................. A61B 3/10
[52] U.S. Cl. ................................... 351/211; 351/210
[58] Field of Search ................. 351/209, 210, 211, 212

[56] References Cited

U.S. PATENT DOCUMENTS 4,264,152 4/1981 Crane .................................. 351/211

Primary Examiner—Rodney B. Bovernick
Assistant Examiner—Paul Dzierzynski
Attorney, Agent, or Firm—John P. Taylor

[57] ABSTRACT

A system is provided for producing a stabilized visual scotoma or aperture which comprises means for projecting the image of a visual scene along a first optical path including first and second mirrors positioned serially along the optical path. Both mirrors are mounted for rotation about an axis corresponding, respectively, to horizontal and vertical eye movements. Optical means are provided for forming an image of the eye at each of the first and second mirror with the center of rotation of the eye in each image nominally at the axes of rotation of the first and second mirrors. Control means are provided to rotate the first and second mirrors about their axes in response to eye movements. Means are provided to project an image of the scene along a second optical path to the eye of the subject including means capable of negating the compensating effect for eye movement in the first optical path. An obscuration member, which may be either an aperture or an opaque target, is positioned between the first optical path and the second optical path to respectively form an aperture or a scotoma of predetermined size and/or shape on the retina which is stabilized with respect to eye movement while the remainder of the visual scene is not.

11 Claims, 5 Drawing Figures

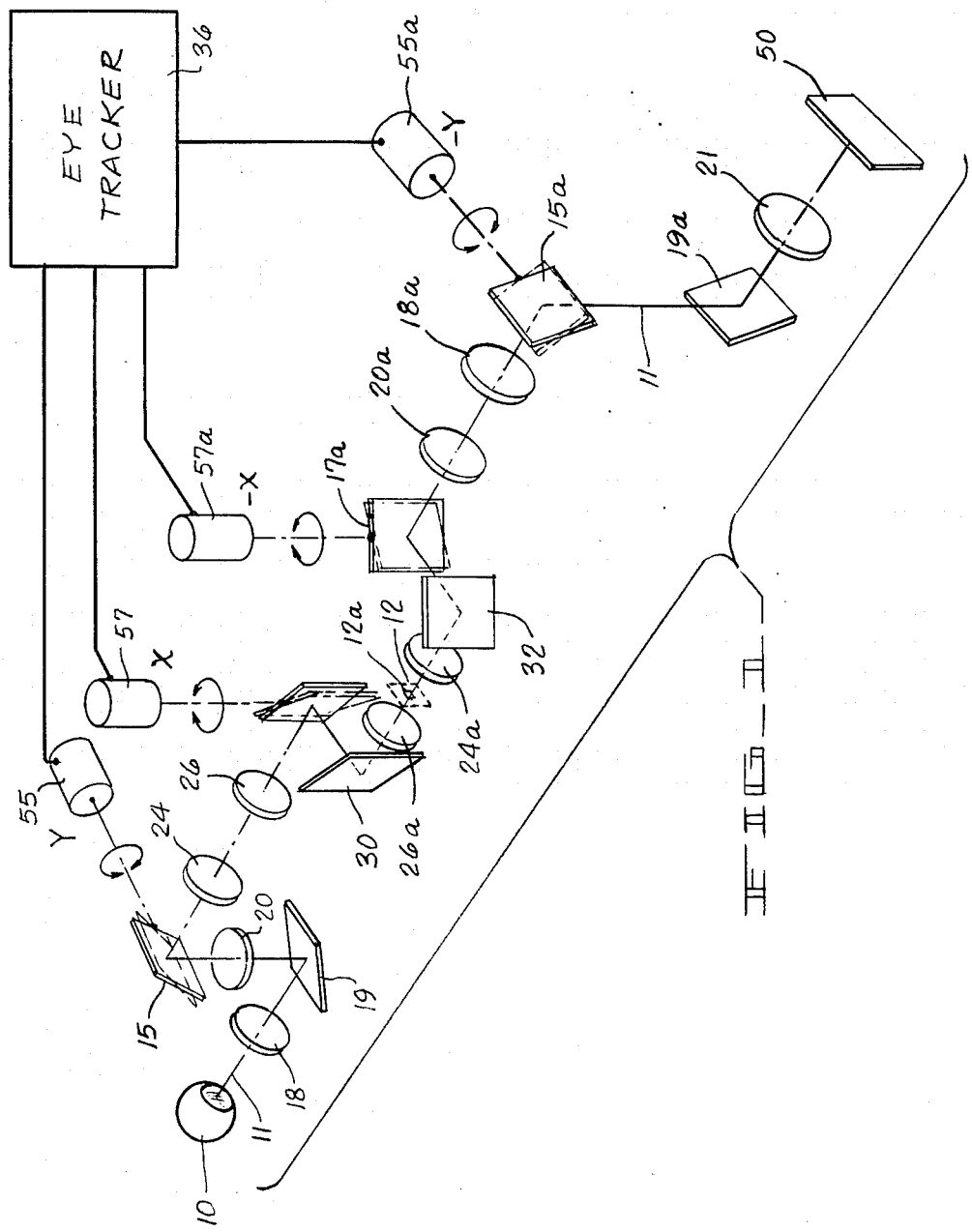

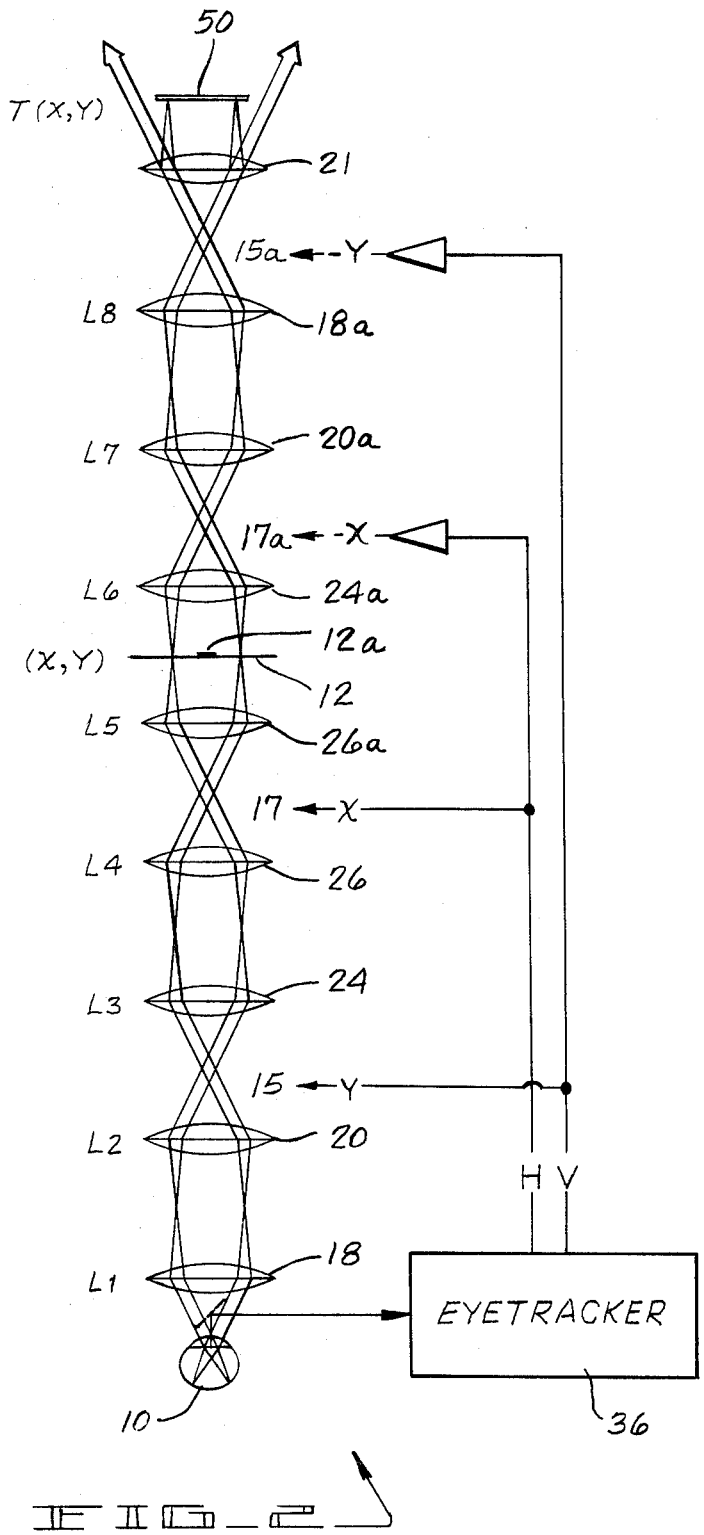

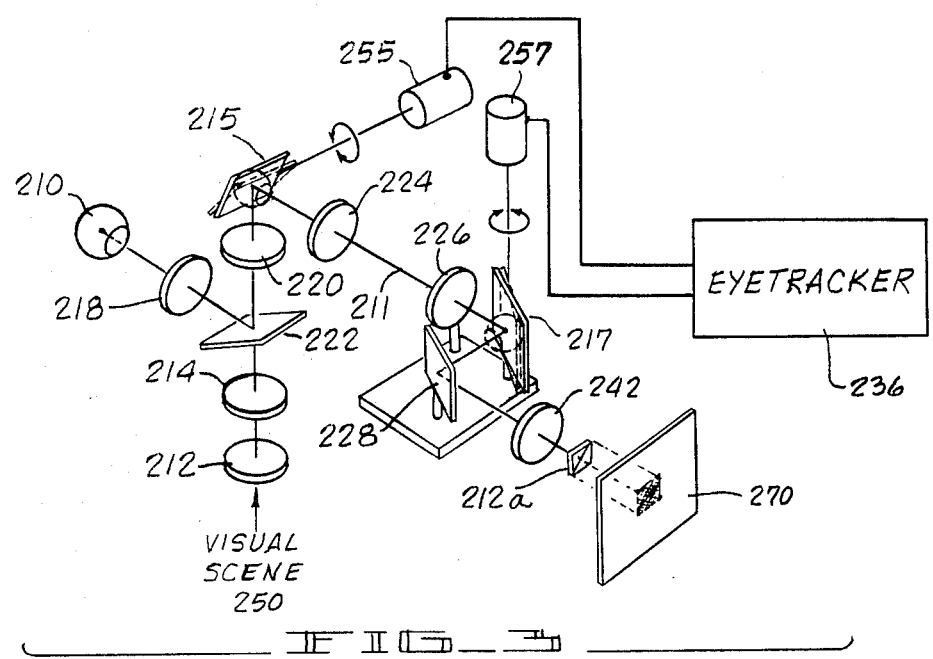
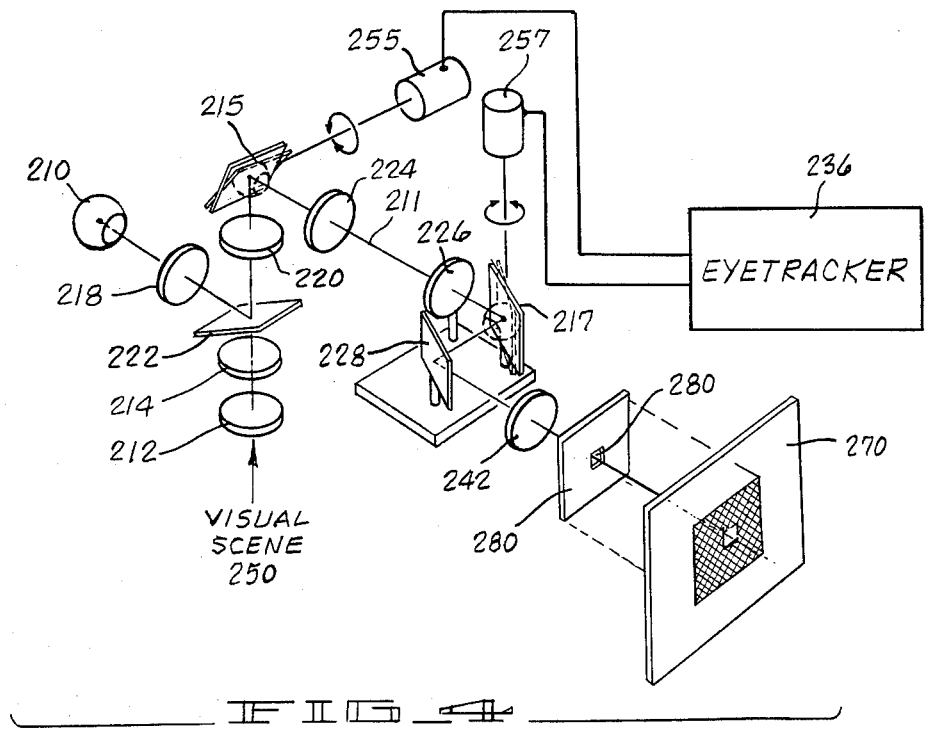

SYSTEM FOR PRODUCING SELECTIVE STABILIZATION OF A PORTION OF THE RETINAL IMAGE

BACKGROUND OF THE INVENTION

1. Origin of Invention

This invention disclosure described herein was made in the course of or under National Institute of Health grants EY-01128 and EY-01031 with the United States Department of Health and Human Services.

2. Technical Field of the Invention

This invention relates to selective stabilization of a portion of the visual field. More particularly, the invention relates to the stabilization of an obscuration such as an aperture or scotoma on a portion of the retina.

3. Background Art

One of the functions of eye movement is to aid the production of visual responses by continuously changing the stimulus on the retina since visual neurons rarely respond to a steady, unchanging pattern. For purposes of studying the functioning of the human visual system, however, it is often desirable to stabilize the perceived image by compensating for such eye motion. For example, in Crane U.S. Pat. No. 4,264,152, a visual stimulus deflector is disclosed in which a target is viewed through an optical path which includes a mirror which can be rotated around a horizontal axis by a servo motor and a second mirror which can be rotated around a vertical axis by a servo motor. Movement of the eye can be compensated for by activation of the horizontal and/or vertical servo motors so that the target is perceived in the same manner as if the eye had not moved. Thus, the target would appear to be stabilized—or not moving— despite movement of the eye.

This stabilization procedure may be automated using an eye tracker which senses horizontal and vertical movement of the eye and sends an appropriate signal to the horizontal and vertical servo motors in the deflector system to adjust the respective mirror to compensate for the eye movement.

Eye tracker systems useful for this purpose are disclosed, for example, in Cornsweet et al U.S. Pat. No. 3,724,932; Crane et al U.S. Pat. No. 3,804,496; and Cornsweet et al U.S. Pat. No. 3,712,716. In these devices, movements of a beam of light reflected from the eye are tracked to indicate the changes in orientation of the optical axis of the eye. Output signals from such devices can be used to record eye movements or to control devices, such as the deflector described above.

While stabilization of the entire visual field provides a useful tool for ophthalmic research, selective stabilization of only a portion of the visual field is also of interest.

In particular, if the subject's visual field were partially blocked by a spot of arbitrary shape, i.e. an obscuring spot, and the obscuring spot could be stabilized on the subject's retina, one could produce a form of retinal pathology known as a scotoma. Such a "blind spot", as the obscuring spot would produce, occurs naturally in the normal eye in the region of no response located at the optic disc. The blind spot is not perceived as a hole in the visual field, but instead appears to be filled with a stimulus similar to whatever surrounds it. Scotomas resulting from retinal disease often "fill in" in this way, in which case they are difficult to identify and map.

Even the normal, healthy retina is far from homogeneous in its properties. In particular, the spatial and chromatic aspects of visual responses vary dramatically with eccentricity. To study these variations, it would be helpful to be able to block off precise, selected regions of the retina, with no interference from eye movements. Thus, the ability to produce artificial scotomas of any desired size, shape, or chromatic characteristics would have important applications in ophthalmic studies.

Such an artificial scotoma could be produced using a modification of the visual stimulus deflector of U.S. Pat. No. 4,264,152 discussed above. The deflector would be modified by placing a transparency containing the stimulus pattern in the image plane nearest the subject. An opaque spot on a transparent plate located in the stabilized image plane would then be viewed through the entire optical path. If the deflector was used with an eye tracker to control the deflector mirrors, the spot would be stabilized with respect to the retina, but the stimulus pattern would not be. The stabilized scotoma pattern, which could be self luminous, a transparency, or a reflection target would, in effect, be imaged on the unstabilized transparency. Thus, the subject would view the stimulus pattern in a normal way except that there would be no illumination of the area corresponding to the image of the spot, and this black shadow would be locked in place on his retina.

However, such a system would have several disadvantages. First, the luminance level within the scotoma region could not be varied; it would always have to be zero in order to completely block the corresponding region of the stimulus. Second, the stimulus pattern would have to be a transparency; it could not be a CRT or a real-world scene.

It would be desirable to be able to produce a stabilized scotoma or obscuring spot while using a real world background to provide the stimulus pattern. It would further be desirable to be able to vary the luminance level within the scotoma.

SUMMARY OF THE INVENTION

It is, therefore, an object of the invention to provide a system for producing selective stabilization of a portion of the retinal image.

It is another object of the invention to provide an artificial scotoma on the retina which may be varied in luminance level, size, shape, and location.

It is yet another object of the invention to provide a stabilized obscuring spot with an unstabilized stimulus pattern.

It is a further object of the invention to provide a stabilized scotoma on the retina wherein the unstabilized stimulus pattern is a real world scene.

It is a still further object of the invention to provide a system wherein an aperture may be stabilized on a portion of the retina, while the stimulus pattern remains unstabilized.

These and other objects of the invention will be apparent from the description and accompanying drawings. In accordance with the invention, a system is provided for producing a stabilized visual scotoma or aperture which comprises means for projecting the image of the scene along a first portion of an optical path including first and second mirrors positioned serially along the optical path, each of the mirrors being mounted for rotation about an axis therethrough. Optical means are provided for forming an image of the eye at each of the first and second mirrors with the center of rotation of the eye in each image nominally at the axes of rotation of the respective first and second mirrors. Control means are provided to respectively rotate the first and second mirrors about their axes in response to movement of the eye. Means are provided for projecting an image of at least a portion of the scene along a second portion of the optical path to the eye of the subject including means capable of negating the compensating effect for eye movement in the first portion of the optical path. An obscuration member, which may be either an aperture or a target of preselected shape and size, is positioned between the first portion of the optical path and the second portion of the optical path to form a scotoma or obscuring spot on the retina which is stabilized with respect to eye movement.

BRIEF DESCRIPTION OF THE DRAWINGS

FIG. 1 is a perspective and partially schematic view illustrating the elements of one embodiment of the system of the invention.

FIG. 2 is a two-dimensional schematic view similar to the embodiment shown in FIG. 1.

FIG. 3 is a perspective and partially schematic view of a preferred embodiment of the invention capable of forming a stabilized scotoma.

FIG. 4 is a perspective and partially schematic view of a preferred embodiment of the invention capable of forming a stabilized aperture.

DESCRIPTION OF THE INVENTION

Figure 5:
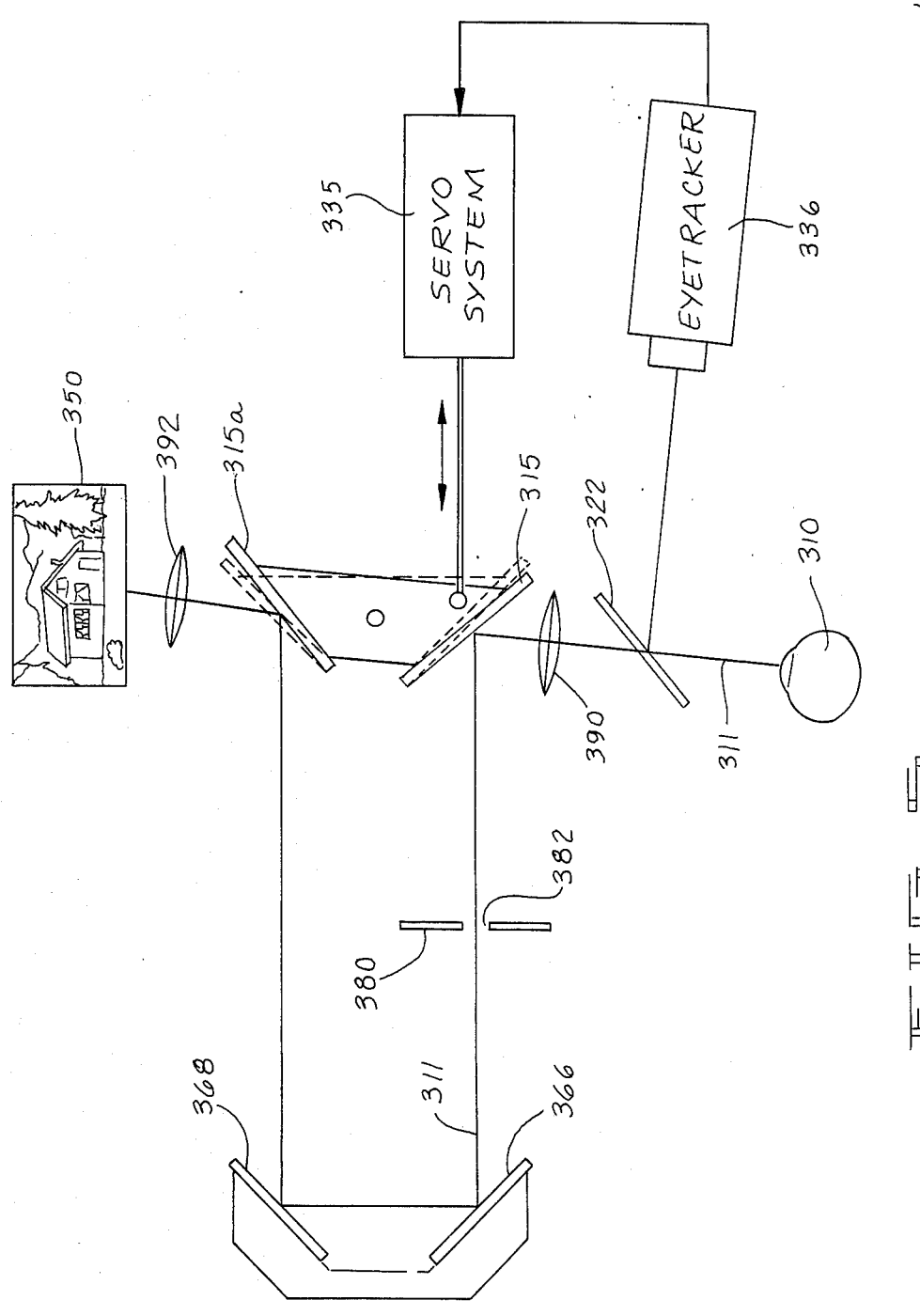
FIG. 5 is a two-dimensional view of yet another embodiment of the invention.

Turning now to FIGS. 1 and 2, the invention is generally illustrated in its broadest aspect. The system is illustrated in three dimensional form in FIG. 1 and, for simplicity, in two dimensional form in FIG. 2. In this embodiment, the scene or target 50 is viewed by the eye 10 through two deflector optical systems (containing four servo controlled mirrors) arranged in tandem. The image of the eye 10 at vertical deflection mirror 15 may be formed by a pair of relay lenses 18 and 20 separated by the sum of their focal lengths and located nominally a focal length from the eye 10 and the axis of rotation of mirror 15 and separated by direction-changing mirror 19. An image of the eye 10 formed at a horizontal deflection mirror 17 is provided by a second pair of identical relay lenses 24 and 26 which are also separated by the sum of their focal lengths and respectively located nominally a focal length from the axis of rotation of vertical deflection mirror 15 and horizontal deflection mirror 17.

In this embodiment of the invention, the image is then transmitted via a pair of direction-changing mirrors 30 and 32 to a third deflection mirror 17a through a third pair of relay lenses 26a and 24a which are similarly positioned with respect to their focal lengths. The horizontal deflection mirror 17a is controlled by the same means controlling the horizontal deflection mirror 17 except that mirror 17a moves in exactly the opposite direction of rotation to cancel out the effect of any movement of deflection mirror 17. The image is then formed again at mirror 15a through a fourth pair of relay lenses 20a and 18a. Mirror 15a represents a vertical deflection mirror disposed to exactly cancel out the movement of vertical deflection mirror 15. Another direction changing mirror 19a is illustrated in FIG. 1 as situated between deflection mirror 15a and target 50.

An optional lens 21 can also be inserted before target 50 for a close-up target.

Mirrors 15, 17, 17a, and 15a are controlled by an eye tracker 36 which forms no part of the present invention. This eye tracker detects movement of the eye and sends appropriate signals to servo motors 55, 57, 57a and 55a (shown only in FIG. 1) which respectively control the movement of the mirrors 15 and 17 and the cancelling out mirrors 17a and 15a. Thus, the target at position 50 will be perceived by the eye at 10 just as if the eye tracker and the deflection mirrors under its control did not exist.

However, in accordance with the invention, a scotoma-producing spot or an aperture may be introduced into the optical path between lenses 26a and 24a, dividing the optical path into a first portion and a second portion. This is illustrated in FIGS. 1 and 2 as a transparency 12 which contains an opaque spot 12a. The image of the opaque spot, unlike the image of the target 50, is affected only by deflection mirrors 15 and 17 in the first portion of the optical path. Thus, the effects of movement of deflection mirrors 15 and 17, based on eye movement, are not cancelled out with respect to the image of the spot 12a by movement of mirrors 15a and 17a. Therefore, spot 12a will be stabilized on the retina while target 50 moves normally on the retina in response to eye movements. While the foregoing system will provide a stabilized scotoma on the retina in accordance with the invention, the double system of lens and mirror deflection, used to permit the stimulus pattern to be viewed normally, leaves much to be desired. More particularly, the cancellation effect of deflection mirrors 15a and 17a must be precisely the same, respectively, as mirrors 15 and 17 to permit the cancellation effect to work properly. It would be a difficult feat of electro-mechanical design in construction to achieve this condition so perfectly that no residual jitter of the stimulus pattern could be detected by the subject. Thus, the illustrated embodiment while exemplifying the goals of the invention is not the preferred mode for carrying out these goals.

Turning now to FIG. 3, a preferred embodiment of the system of the invention is illustrated in three dimensional form. The visual scene depicted as 250 passes through lens 214 to a beam splitter 222 and lens 220 to a vertical deflection mirror 215 thence through a pair of relay lenses 224 and 226 to horizontal deflection mirror 217. The image is then reflected from mirror 228 through lens 242 to mirror 270 which is positioned with its plane normal to the beam 211 and conjugate to the retina.

This permits the first and second portions of the optical path shown in FIGS. 1 and 2 to be "folded" into a single system through which the unobscured portion of the scene image makes two passes in opposite directions to arrive at the retina in its normal, unstabilized, state. A target spot 212a of predetermined size and shape to provide a particular scotoma on the retina is positioned on mirror 270. It should be noted here that spot 212a is shown in FIG. 3 as projected off mirror 270 for illustrative purposes only, it being understood that spot 212a is nominally in the same plane as mirror 270. The visual scene is reflected back through the optical path just described but is reflected off beam splitter 222 through lens 218 to the eye 210. Thus, visual scene 250 passes through optical path 211 twice with the second portion of the optical path or reverse path resulting in movements of the horizontal and vertical position deflection mirrors being cancelled out for the visual scene. The spot 212a, however, only passes through the system once; and, thus, the spot is stabilized on the retina by the compensating movements of mirrors 215 and 217.

Mirrors 215 and 217 are respectively controlled by eye tracker 236 through servo motors 255 and 257. Thus, vertical movement of the eye as perceived by eye tracker 236 results in a signal being sent to servo motor 255 to rotate mirror 215 to compensate for the eye movement. Likewise horizontal eye movement as detected by eye tracker 236 results in a signal being sent to servo motor 257 to rotate mirror 217 to compensate for the horizontal movement of the eye.

In FIG. 4, a modification of the embodiment of FIG. 3 is illustrated. In this embodiment, an aperture, rather than a scotoma, is stabilized on the retina. An opaque member 280, containing an aperture 282 of predetermined size and shape, is affixed to mirror 270 (shown in FIG. 4 as projected off mirror 270 for illustrative purposes only). The portion of the visual scene 250 which passes through aperture 282 (and is reflected back from mirror 270 through optical path 211 to the eye 210) is, thus, a normal, unstabilized visual scene due to the cancelling out effect of the movement of deflection mirrors 215 and 217 as previously discussed with regard to FIG. 3. It should be noted here that the obscuring spot or aperture must be in a plane conjugate to the retina as is also true of mirror 270. If the obscuration was not in a plane conjugate to the retina, the obscuration would be out of focus.

However, the outline of aperture 282, since it does not traverse the optical path twice as does the visual scene, thus remains fixed on a portion of the retina despite eye movement. Thus, eye movement would permit visibility of a different portion of the visual scene, but it would be perceived by the same portion of the retina due to the stabilization of aperture 282 thereon.

Yet another embodiment is illustrated in FIG. 5 in which a servo-driven deflection mirror 315 is rigidly coupled to a second deflection mirror 315a and controlled by eye tracker 336 through servo system 355 to provide stabilization for eye movement in one axis such as the Y axis (Vertical). The optical path 311 from the eye 310 through beam splitter 322 and through lens 390 is reflected by deflection mirror 315 to a stationary mirror 366 and then to a second stationary mirror 368 where it is reflected to deflection mirror 315a. The optical path passes through an aperture 382 in an opaque member 380 which is placed in optical path 311 after deflection mirror 315 and at the focal plane of lens 390 so that it is in focus on the retina. A lens 392 is positioned between mirror 315a and image 350 so that target 350 is imaged in the plane of aperture 380 which will make it focus on the retina as well.

Thus, eye movement by eye 310, which is compensated for by the eye tracker's control over deflection mirror 315, is cancelled out by the identical movement of deflection mirror 315a. However, aperture 382, which is only reflected by mirror 315, is stabilized on the retina of eye 310. It should be pointed out, though, that this embodiment provides only one-dimensional stabilization. That is, it can compensate for either horizontal or vertical eye movements, but not both.

It should be noted that opaque member 380 containing aperture 382 could be replaced by a transparency containing an opaque spot if it was desired instead, in this embodiment, to stabilize an obscuring spot or scotoma on the retina, as previously discussed with regard to the other embodiments.

The use of the term obscuration herein is intended to include any partial obscuring of the visual scene to form a stabilized portion on a region of the retina including both the obscuring spot and aperture modes of the invention.

Thus, the invention provides novel means for providing an obscuration in the form of either a stabilized aperture or an obscuring spot (scotoma) on the retina while using an unstabilized real world scene as the visual stimulus for the retina. Minor modifications may be apparent from the foregoing description and drawings without departing from the scope of the invention which is to be limited only by the scope of the appended claims.

Having thus described the invention, what is claimed is:

1. A system capable of producing a stabilized obscuration on a retina which comprises: means for projecting the image of a visual scene along a first portion of an optical path, including first and second mirrors positioned serially along the optical path, each of said mirrors being mounted for rotation about an axis corresponding respectively to horizontal and vertical eye movements, optical means for forming an image of the eye at each of the first and second mirrors, with the center of rotation of the eye in each image nominally at the axes of rotation of the said first and second mirrors, first and second control means to respectively rotate the said first and second mirrors about their axes in response to movement of the eye, means for projecting at least a portion of the scene image along a second portion of said optical path to the eye of a subject, including means capable of negating the compensating effect for eye movement in said first portion of said optical path and a member of preselected shape and size positioned between said first portion of said optical path and said second portion of said optical path to form an obscuration on the retina which is stabilized with respect to eye movement.

2. The system of claim 1 wherein said member of predetermined size and shape comprises an opaque spot in the optical path and said opaque spot is stabilized on some part of the retina.

3. The system of claim 1 wherein said member of predetermined size and shape comprises an aperture and said aperture is stabilized on the retina.

4. The system of claim 1 wherein said means for projecting the scene image along said second portion of said optical path comprises a mirror which reflects the scene image back through the said optical path whereby said second portion of said optical path is superimposed on said first portion of said optical path and said means for negating the compensating effect for eye movement comprises the same first and second mirrors whose rotation about their axes move the second portion of said optical path in a manner which cancels out the effect of movement within said first portion of said optical path whereby the visual scene is not stabilized except for said stabilized obscuration which traverses only said second portion of said optical path.

5. The system of claim 4 wherein said mirror for reflecting the scene image back through the said optical path has said obscuration mounted thereon whereby only a portion of said visual image scene is reflected back through the same optical path.

6. The system of claim 5 wherein said obscuration is an opaque spot mounted on said mirror for reflecting the image scene back through the same optical path.

7. The system of claim 5 wherein said obscuration is an aperture mounted on said mirror for reflecting the image scene back through the same optical path.

8. The system of claim 1 wherein said second portion of said optical path comprises a series of mirrors including, respectively, mirrors capable of rotating about the same axes as said rotating mirrors in said first portion of said optical path and said means negating the compensating effect in said first portion of said optical path comprise means for rotating said mirrors in said second portion of said optical path in the opposite direction of the rotation of said rotating mirrors in said first portion of said optical path whereby the stabilizing effect of said movement in the first portion of said optical path is cancelled out for the unobscured portion of the visual scene traversing both portions of said optical path.

9. The system of claim 1 wherein said rotatable mirrors in said first portion of said optical path are coupled, respectively, to rotatable mirrors in said second portion of said optical path whereby any compensating rotation of the mirrors in said first portion of said optical path for eye movement will be cancelled out by simultaneous movement of said mirrors in said second portion of said optical path for the scene imaged along both portions of said optical path.

10. A system capable of producing a stabilized obscuration on a retina which comprises:
  (a) means for projecting the image of a visual scene along a first portion of an optical path, including:
    (1) first and second mirrors positioned serially along the optical path, each of said mirrors being mounted for rotation about an axis corresponding respectively to horizontal and vertical eye movements; and
    (2) optical means for forming an image of the eye at each of the first and second mirrors, with the center of rotation of the eye in each image nominally at the axes of rotation of the said first and second mirrors;
  (b) first and second control means to respectively rotate the said first and second mirrors about their axes in response to movement of the eye;
  (c) reflective means for projecting at least a portion of the scene image back along the same optical path in a reverse direction to the eye of a subject whereby a second portion of said optical path is superimposed on said first portion of said optical path to thereby negate the compensating effect for eye movement in said first portion of said optical path; and
  (d) means of preselected shape and size positioned between said first portion of said optical path and said second portion of said optical path for forming an obscuration on the retina which is stabilized with respect to eye movement.

11. The system of claim 10 wherein said reflective means comprise a mirror for reflecting the scene image back through the said optical path; and said mirror for reflecting the scene image back through the same optical path has said means for forming an obscuration mounted thereon; whereby only a portion of said visual image scene is reflected back through the same optical path.

* * * * *